(12) United States Patent
Kamata et al.

(10) Patent No.: US 7,935,483 B2
(45) Date of Patent: May 3, 2011

(54) METHOD OF EFFECTING LYSIS OF ACID-FAST BACTERIA AND METHOD OF PERFORMING GENE AMPLIFICATION OR DETECTION THEREWITH

(75) Inventors: Tatsuo Kamata, Kyoto (JP); Yuji Izumizawa, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 600 days.

(21) Appl. No.: 11/656,575

(22) Filed: Jan. 23, 2007

(65) Prior Publication Data

US 2007/0178508 A1 Aug. 2, 2007

Related U.S. Application Data

(62) Division of application No. 10/500,435, filed as application No. PCT/JP03/06321 on May 21, 2003, now abandoned.

(30) Foreign Application Priority Data

May 21, 2002 (JP) ................................ 2002-146823
Jun. 24, 2002 (JP) ................................ 2002-183461

(51) Int. Cl.
*C12Q 1/68* (2006.01)
(52) U.S. Cl. ............................................................ 435/6
(58) Field of Classification Search .................... None
See application file for complete search history.

(56) References Cited

U.S. PATENT DOCUMENTS

| 5,712,095 | A | 1/1998 | Britschgi et al. |
| 6,251,659 | B1 | 6/2001 | Fukuzuno et al. |
| 6,979,450 | B2 | 12/2005 | Nakamura |

FOREIGN PATENT DOCUMENTS

| EP | 0 547 789 | 3/1993 |
| JP | 9-178752 | 7/1997 |
| JP | 10-304869 | 11/1998 |
| JP | 11-263736 | 9/1999 |
| WO | 95/14768 | 6/1995 |

OTHER PUBLICATIONS

Whipple et al. (J Clin Microbiol. Aug. 1987;25(8):1511-5).*
Folgueira et al. (J Clin Microbiol. Apr. 1993;31(4):1019-21).*
Sritharan et al. (Mol Cell Probes. Oct. 1991;5(5):385-95).*
Whipple D. L. et al. "Isolation and Analysis of Restriction Endonuclease Digestive Patterns of Chromosomal DNA from *Mycobacterium* Species". Journal of Clinical Microbiology, Aug. 1987, vol. 25, No. 8, p. 1511-1515.
Sritharan, et al., "A simple method for diagnosing *M. tuberculosis* infection in clinical samples using PCR", Molecular and Cellular Probes (1991) 5, 385-395.
Folgueria, et al., "Detection of *Mycobacterium tuberculosis* DNA in Clinical Samples by using a Simple Lysis Method and Polymerase Chain Reaction", Journal of Clinical Microbiology, Apr. 2003, vol. 31, No. 4, pp. 1019-1021.
Pierre, et al., "Use of a reamplification protocol improves sensitivity of detection of *Mycobacterium tuberculosis* in clinical samples by amplification of DNA", J Clin Microbio. Apr. 1991, 29(4): 712-7.

* cited by examiner

*Primary Examiner* — Christopher M. Babic
(74) *Attorney, Agent, or Firm* — Morgan Lewis & Bockius LLP

(57) ABSTRACT

A method of effecting lysis of acid-fast bacteria, comprising heating acid-fast bacteria in a liquid containing a non-ionic surfactant at a temperature of below the boiling point of the liquid. This method enables accomplishing secure lysis of acid-fast bacteria in a simple manner within a short period of time without the use of special apparatus and agent and enables extracting genes. The heating is preferably conducted at 96° C. for 10 min. As the nonionic surfactant, use can be made of a d-sorbitol fatty acid ester, a polyoxyethylene glycol sorbitan alkyl ester, a polyoxyethylene glycol p-t-octylphenyl ether or the like. The pH value of the liquid is preferably 8, and the liquid preferably contains EDTA. It is also preferred that before the heating, the acid-fast bacteria be treated with lipase.

13 Claims, 3 Drawing Sheets

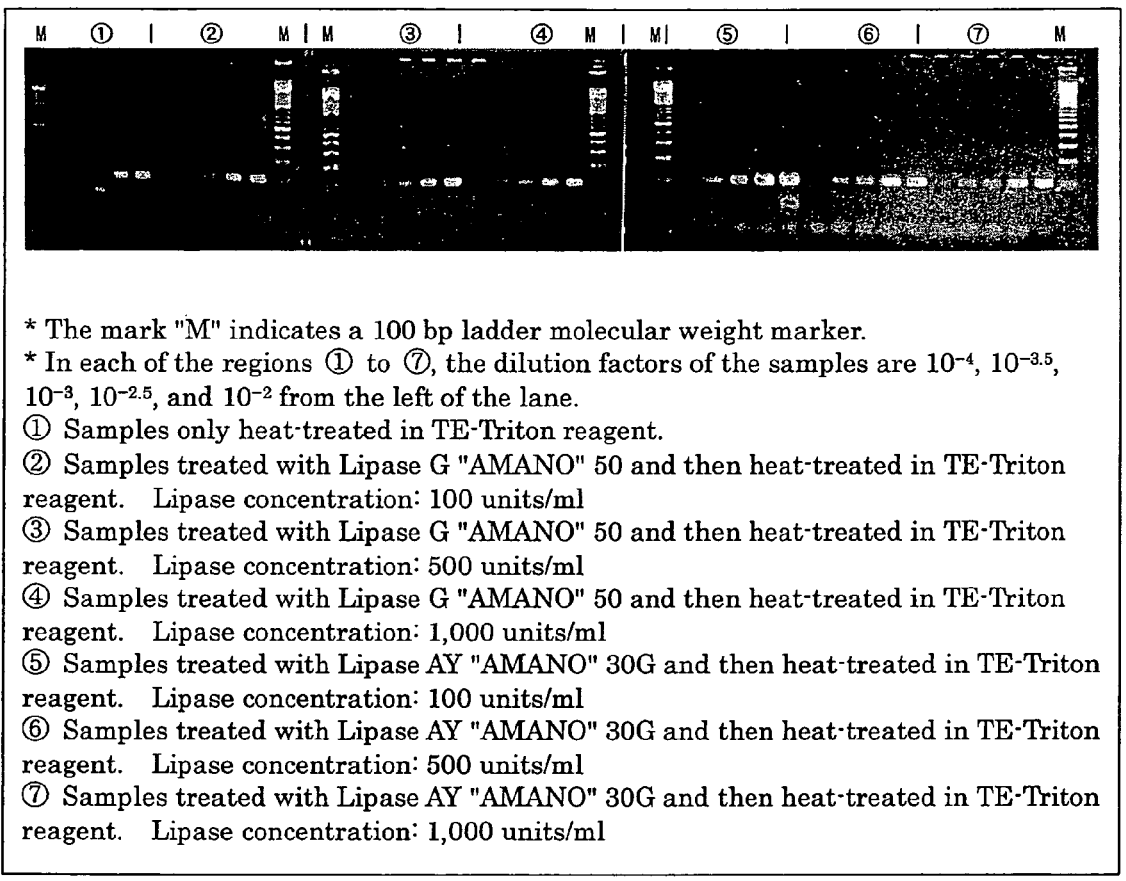

* The mark "M" indicates a 100 bp ladder molecular weight marker.
* In each of the regions ① to ⑦, the dilution factors of the samples are $10^{-4}$, $10^{-3.5}$, $10^{-3}$, $10^{-2.5}$, and $10^{-2}$ from the left of the lane.
① Samples only heat-treated in TE-Triton reagent.
② Samples treated with Lipase G "AMANO" 50 and then heat-treated in TE-Triton reagent. Lipase concentration: 100 units/ml
③ Samples treated with Lipase G "AMANO" 50 and then heat-treated in TE-Triton reagent. Lipase concentration: 500 units/ml
④ Samples treated with Lipase G "AMANO" 50 and then heat-treated in TE-Triton reagent. Lipase concentration: 1,000 units/ml
⑤ Samples treated with Lipase AY "AMANO" 30G and then heat-treated in TE-Triton reagent. Lipase concentration: 100 units/ml
⑥ Samples treated with Lipase AY "AMANO" 30G and then heat-treated in TE-Triton reagent. Lipase concentration: 500 units/ml
⑦ Samples treated with Lipase AY "AMANO" 30G and then heat-treated in TE-Triton reagent. Lipase concentration: 1,000 units/ml

FIG. 1

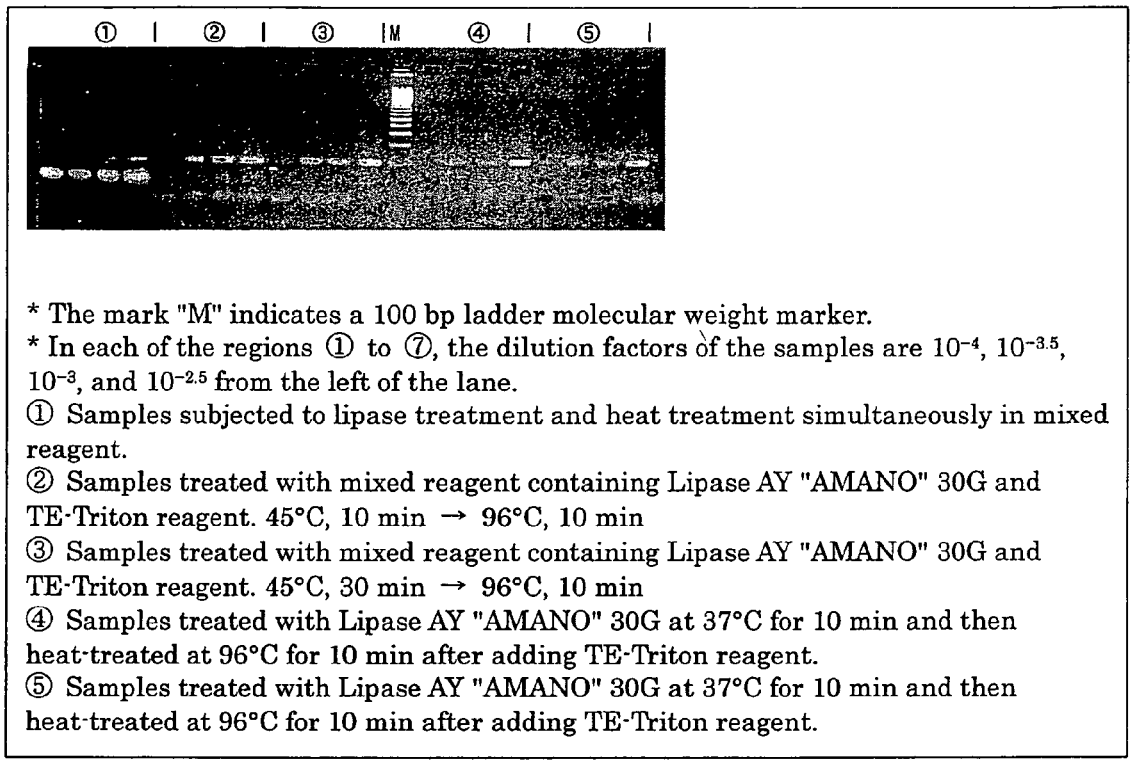

\* The mark "M" indicates a 100 bp ladder molecular weight marker.
\* In each of the regions ① to ⑦, the dilution factors of the samples are $10^{-4}$, $10^{-3.5}$, $10^{-3}$, and $10^{-2.5}$ from the left of the lane.
① Samples subjected to lipase treatment and heat treatment simultaneously in mixed reagent.
② Samples treated with mixed reagent containing Lipase AY "AMANO" 30G and TE-Triton reagent. 45°C, 10 min → 96°C, 10 min
③ Samples treated with mixed reagent containing Lipase AY "AMANO" 30G and TE-Triton reagent. 45°C, 30 min → 96°C, 10 min
④ Samples treated with Lipase AY "AMANO" 30G at 37°C for 10 min and then heat-treated at 96°C for 10 min after adding TE-Triton reagent.
⑤ Samples treated with Lipase AY "AMANO" 30G at 37°C for 10 min and then heat-treated at 96°C for 10 min after adding TE-Triton reagent.

FIG. 2

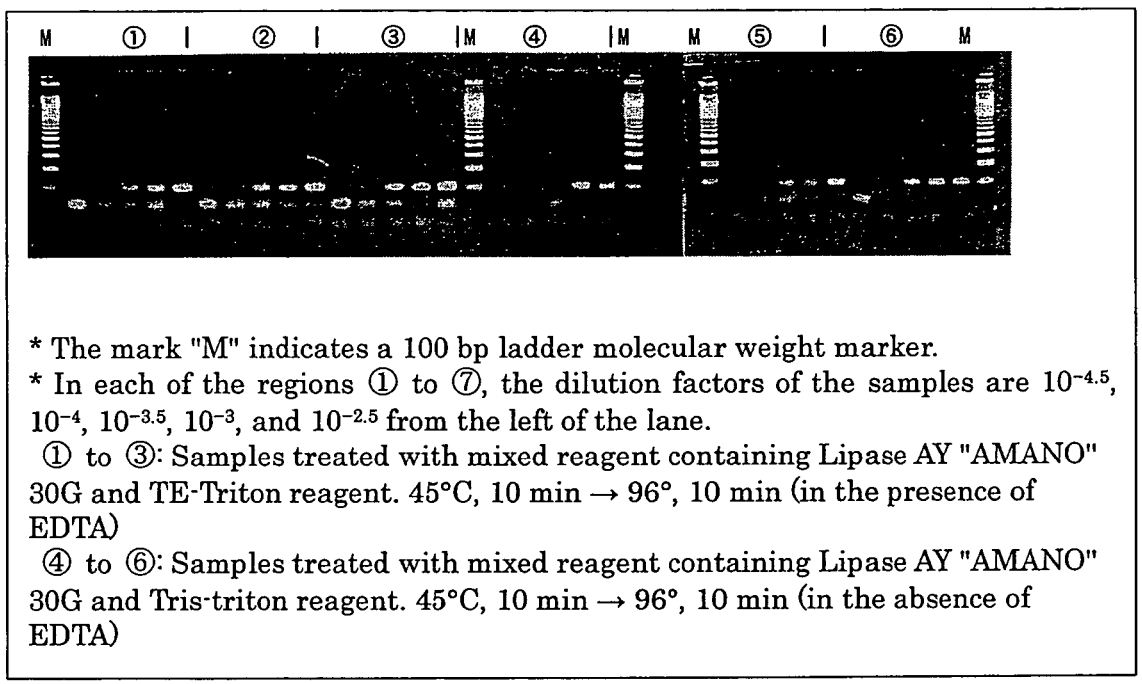

* The mark "M" indicates a 100 bp ladder molecular weight marker.
* In each of the regions ① to ⑦, the dilution factors of the samples are $10^{-4.5}$, $10^{-4}$, $10^{-3.5}$, $10^{-3}$, and $10^{-2.5}$ from the left of the lane.

① to ③: Samples treated with mixed reagent containing Lipase AY "AMANO" 30G and TE-Triton reagent. 45°C, 10 min → 96°, 10 min (in the presence of EDTA)

④ to ⑥: Samples treated with mixed reagent containing Lipase AY "AMANO" 30G and Tris-triton reagent. 45°C, 10 min → 96°, 10 min (in the absence of EDTA)

FIG. 3

METHOD OF EFFECTING LYSIS OF ACID-FAST BACTERIA AND METHOD OF PERFORMING GENE AMPLIFICATION OR DETECTION THEREWITH

CROSS REFERENCE TO RELATED APPLICATIONS

This application is a Division of application Ser. No. 10/500,435, filed Jun. 28, 2004, which is a U.S. National Stage of application no. PCT/JP03/06321, filed May 21, 2003, which application is incorporated herein by reference.

TECHNICAL FIELD

The present invention relates to a method of lysing acid-fast bacteria and to a method of performing gene amplification or gene detection using the same.

BACKGROUND ART

Tuberculosis still is a serious bacterial disease worldwide, and not only treatment methods but also diagnostic methods therefor are extremely important. A final diagnosis as to the tuberculosis infection is made by carrying out a culture method. However, since tubercule bacilli have an extremely slow growth rate, the establishment of a preliminary diagnostic method to be performed prior to the culture method has been desired. As such a preliminary diagnostic method, a method using a polymerase chain reaction (PCR) method is attracting attention. In this method, a primer specific to a gene of a tubercule bacillus is used to amplify a gene of the tubercule bacillus, if any, so that it can be detected, thereby enabling the presence or absence of the tubercule bacillus to be determined.

In the above-described preliminary diagnostic method using the PCR method, extracting the gene by lysing the tubercule bacillus is necessary as a pretreatment. Examples of conventional lysis methods include chemical methods using organic solvents or the like and physical methods using ultrasonic waves or repeating freezing and thawing. However, since tubercule bacilli have a high cell-wall lipid content, such conventional lysis methods cannot extract genes sufficiently. In order to achieve sufficient gene extraction, it is necessary to make the treatment conditions severer, which requires the use of a special device and/or a special reagent. Besides, this may result in a longer treatment period and a more complicated operation. Such problems with lysing are not specific to tubercule bacilli and relate to the entire acid-fast bacteria group including the tubercule bacilli.

DISCLOSURE OF INVENTION

Therefore, with the foregoing in mind, it is an object of the present invention to provide a method of lysing acid-fast bacteria easily and in a short time without using any special device or special reagent.

In order to achieve the above object, a first lysis method of the present invention is a method of lysing an acid-fast bacterium to extract a gene from the acid-fast bacterium, including: heating the acid-fast bacterium in a liquid containing a non-ionic detergent at a temperature below a boiling point of the liquid.

Furthermore, in order to achieve the above object, a second lysis method of the present invention is a method of lysing an acid-fast bacterium to extract a gene from the acid-fast bacterium, including: causing lipolysis by treating the acid-fast bacterium with lipase, and heating the acid-fast bacterium in the presence of a non-ionic detergent.

According to the first lysis method of the present invention, a gene can be extracted sufficiently from an acid-fast bacterium by merely heating the acid-fast bacterium in a solution containing a non-ionic detergent, for example, at 96° C. for 10 minutes. Thus, a method of amplifying or detecting the gene to be performed subsequently can be carried out easily. Furthermore, since the heating temperature is below the boiling point of the liquid, the method has the following advantages, for example. Since the bumping of the liquid is prevented, there is reduced concern that a sample might be scattered. Moreover, since the temperature can be controlled easily, a special heater is not necessary.

On the other hand, the inventors of the present invention achieved the second lysis method of the present invention by focusing on the fact that acid-fast bacteria have a high cell-wall lipid content. That is, in the second lysis method of the present invention, a cell wall of an acid-fast bacterium is weakened by the lipolysis and the acid-fast bacterium is lysed by the heating.

According to the first and second lysis methods of the present invention, acid-fast bacteria can be lysed easily and in a short time without using any special reagent such as a chaotropic reagent or any special device such as an ultrasonic device. Besides, since the first and second lysis methods are chemical methods, they can be carried out safely with little risk that a sample might be scattered. Moreover, according to the first and the second lysis methods of the present invention, the gene extracted may be subjected to a gene amplification process or a gene detection process as it is without being purified. It is to be noted that the first and the second lysis methods of the present invention are applicable not only to a method of performing gene amplification or gene detection but also to other fields such as gene manipulation, for example.

BRIEF DESCRIPTION OF DRAWINGS

FIG. 1 is a photograph showing the result of the electrophoresis performed to determine a lysing effect of one example of the present invention;

FIG. 2 is a photograph showing the result of the electrophoresis performed to determine a lysing effect of another example of the present invention; and FIG. 3 is a photograph showing the result of the electrophoresis performed to determine a lysing effect of still another example of the present invention.

BEST MODE FOR CARRYING OUT THE INVENTION

Hereinafter, the first lysis method and the second lysis method according to the present invention will be described in further detail.

First, the first lysis method of the present invention will be described.

In the first lysis method of the present invention, the heating temperature preferably is not less than 70° C. and less than 100° C., more preferably not less than 80° C. and less than 100° C., and most suitably 96° C. Furthermore, the heating is performed, for example, for 1 to 30 minutes, preferably for 10 minutes. The pH of the liquid is, for example, in the range from 7.0 to 12.0, preferably 8.0. The concentration of the non-ionic detergent in the liquid is, for example, 0.01 to 10 wt %, preferably 0.5 to 2.0 wt %, and more preferably 1.0 wt %.

Examples of the non-ionic detergent include: D-sorbitol fatty acid esters such as Span 20, Span 40, Span 60, Span 65, Span 80, and Span 85 (all manufactured by Nacalai Tesque, Inc., for example); polyoxyethyleneglycol sorbitan alkyl esters such as Tween 20, Tween 21, Tween 40, Tween 60, Tween 65, Tween 80, Tween 81, and Tween 85 (all manufactured by Nacalai Tesque, Inc., for example); polyoxyethyleneglycol p-t-octylphenyl ethers such as Triton X-100 (manufactured by Nacalai Tesque, Inc., for example). These detergents may be used either alone or in combinations of two or more types. Among these, Triton X-100, Tween 20, and Tween 21 are preferable, and Triton X-100 is more preferable.

In the first lysis method of the present invention, it is preferable that the liquid further contains a metal chelating agent. The metal chelating agent serves to prevent a gene-degrading enzyme such as DNase contained in a sample from degrading the gene, for example. The concentration of the metal chelating agent in the liquid is, for example, 0.1 to 100 mM, preferably 1.0 mM. Examples of the metal chelating agent include ethylenediaminetetraacetic acid (EDTA), ethylene glycol bis(β-aminoethyl ether)-N,N,N',N'-tetraacetic acid (EGTA), diaminocyclohexane tetraacetic acid, o-phenanthroline, and salicylic acid. These metal chelating agents may be used either alone or in combinations of two or more types. Among these, EDTA and EGTA are preferable, and EDTA is more preferable.

Examples of an acid-fast bacterium to which the first lysis method of the present invention is applicable include *M. avium*, *M. intracellularae*, *M. gordonae*, *M. tuberculosis*, *M. kansasii*, *M. fortuitum*, *M. chelonae*, *M. bovis*, *M. scrofulaceum*, *M. paratuberculosis*, *M. phlei*, *M. marinum*, *M. simiae*, *M. szulgai*, *M. leprae*, *M. xenopi*, *M. ulcerans*, *M. lepraemurium*, *M. flavescens*, *M. terrae*, *M. nonchromogenicum*, *M. malmoense*, *M. asiaticum*, *M. vaccae*, *M. gastri*, *M. triviale*, *M. haemophilum*, *M. africanum*, *M. thermroresistable*, and *M. smegmatis*.

In the first lysis method of the present invention, examples of a biological sample containing an acid-fast bacterium include sputum, spinal fluid, feces, saliva, blood, tissues, and urine.

Next, the first lysis method of the present invention can be carried out in the following manner, for example. First, to a buffer having a pH in the above-described predetermined range, a metal chelating agent such as EDTA is added as necessary and a non-ionic detergent further is added, thus preparing a lysis reagent solution. As the buffer, Tris-HCl buffer, HEPES buffer, MOPS buffer, HEPPS buffer, TAPS buffer, phosphate buffer, or the like may be used. This lysis reagent solution preferably is sterilized by high-pressure steam in an autoclave. On the other hand, a sample solution is prepared. For example, a sputum specimen that has been homogenized and sterilized by the N-acetyl-L-cysteine-NaOH method (NALC—NaOH method) or the like may be used as the sample solution. The sample solution is centrifuged and the supernatant is removed. To the remaining precipitate (pellet), the lysis reagent solution is added. Thereafter, a lysis treatment is carried out by heating the mixture at a temperature in the above-described predetermined range using a heating block or the like. Examples of heating means other than the heating block include a water bath, a microwave oven, and an air bath.

The specimen thus lysed may be subjected to a gene amplification process or a gene detection process simply as it is or after being pretreated. Examples of the method of performing the gene amplification or gene detection include a PCR method and modifications of the PCR method, such as a RT-PCR method. Furthermore, examples of the gene to be analyzed include DNA and RNA.

Next, the second lysis method of the present invention will be described.

In the second lysis method of the present invention, it is preferable that the heating also serves to deactivate the lipase. This allows the lipase to be deactivated without performing any special process. In addition, the possibility that the lipase might affect a process to be performed subsequent to the lysis treatment, such as a gene amplification process or a gene detection process, can be eliminated.

In the second lysis method of the present invention, it is preferable that the lipolysis and the heating are performed in buffers, respectively. It is more preferable that the lipolysis and the heating are performed in the same buffer. The type of the buffer is not particularly limited, and for example, Tris buffer, HEPES buffer, phosphate buffer, glycine buffer, McIlvaine buffer, and the like can be used. Among these, Tris buffer and HEPES buffer are preferable.

In the second lysis method of the present invention, it is preferable that the lipolysis and the heating are performed in the same container as a closed system. By performing the lipolysis and the heating in the closed system, it is possible to prevent a sample from being scattered. Moreover, by performing the lipolysis and the heating in the same container, the processing efficiency can be improved.

In the second lysis method of the present invention, the heating may be performed after the lipolysis, or the lipolysis and the heating may be performed simultaneously. In the former case, for example, the lipolysis is performed at a pH of 4 to 8 and at a temperature of 37° C. to 60° C. for 5 to 30 minutes, and the heating is performed at a temperature of 37° C. to 100° C. for 5 to 30 minutes. Preferably, the lipolysis is performed at a pH of 6 to 8 and at a temperature of 37° C. to 50° C. for 5 to 20 minutes, and the heating is performed at a temperature of 80° C. to 100° C. for 5 to 20 minutes. More preferably, the lipolysis is performed at a pH of 6.5 to 7.5 and at a temperature of 37° C. to 50° C. for 10 minutes, and the heating is performed at a temperature of 90° C. to 98° C. for 10 minutes. On the other hand, in the latter case, the lipolysis and the heating are performed, for example, at a pH of 4 to 8 and at a temperature of 37° C. to 60° C. for 10 to 30 minutes; preferably at a pH of 6 to 8 and at a temperature of 37° C. to 50° C. for 10 to 20 minutes, and more preferably at a pH of 6.5 to 7.5 and at a temperature of 45° C. to 50° C. for 10 to 20 minutes.

The concentration of the lipase in the buffer is 10 to 10000 units/ml, preferably 100 to 2000 units/ml, and more preferably 200 to 1000 units/ml. The lipase used is not particularly limited, and for example, products named Lipase R "AMANO" G, Lipase M "AMANO" 10, Lipase G "AMANO" 50, Lipase AY "AMANO" 30G, Lipase A "AMANO" 6 (all manufactured by Amano Pharmaceutical Co., Ltd.) and the like may be used. They may be used either alone or in combinations of two or more types. Among these, Lipase G "AMANO" 50 and Lipase AY "AMANO" 30G are preferable, and Lipase AY "AMANO" 30G is more preferable.

The concentration of the non-ionic detergent in the buffer is, for example, 0.01 to 10 wt %, preferably 0.1 to 2.0 wt %, and more preferably 0.5 to 1.0 wt %.

Examples of the non-ionic detergent include: D-sorbitol fatty acid esters such as Span 20, Span 40, Span 60, Span 65, Span 80, and Span 85 (all manufactured by Nacalai Tesque, Inc., for example); polyoxyethyleneglycol sorbitan alkyl esters such as Tween 20, Tween 21, Tween 40, Tween 60, Tween 65, Tween 80, Tween 81, and Tween 85 (all manufactured by Nacalai Tesque, Inc., for example); polyoxyethyleneglycol p-t-octylphenyl ethers such as Triton X-100 (manufactured by Nacalai Tesque, Inc., for example). These detergents may be used either alone or in combinations of two or more types. Among these, Tween 20 and Triton X-100 are preferable, and Triton X-100 is more preferable.

Preferably, the heating is performed in the presence of a metal chelating agent in addition to the non-ionic detergent. The metal chelating agent serves to prevent a gene-degrading enzyme such as DNase contained in a sample from degrading the gene, for example. The concentration of the metal chelating agent in the liquid is, for example, 0.1 to 2.0 mM, preferably 0.5 to 1.0 mM. Examples of the metal chelating agent include ethylenediaminetetraacetic acid (EDTA), glycol ether diaminetetraacetic acid (EGTA), and 1,2-cyclohexanediaminetetraacetic acid (CyDTA). These metal chelating agents may be used either alone or in combinations of two or more types. Among these, EDTA and EGTA are preferable, and EDTA is more preferable.

The second lysis method is applicable to the same acid-fast bacteria as the first lysis method. Furthermore, biological samples containing an acid-fast bacterium to be used in the second lysis method also are the same as those in the first lysis method.

Next, the second method of the present invention can be carried out in the following manner, for example. First, to a buffer having a pH in the above-described predetermined range, lipase and a non-ionic detergent are added, and a metal chelating agent such as EDTA is added as necessary, thus preparing a lysis reagent solution. This lysis reagent solution preferably is sterilized by high-pressure steam in an autoclave. A sample is added to this lysis reagent solution, and the resultant mixture is incubated at 45° C. for 10 minutes (the lipolysis), and then further incubated at 96° C. for 10 minutes (the heating). A cell wall of the acid-fast bacterium is weakened by the former incubation, and the acid-fast bacterium is lysed and also the lipase is deactivated by the latter incubation. Both of the incubations may be carried out using a heating block, a water bath, a thermal cycler, or the like. Alternatively, the lipolysis and the heating may be performed simultaneously by adding the sample to the lysis reagent solution and then incubating the resultant mixture at a temperature of 37° C. to 50° C. for 10 to 20 minutes.

The sample may be prepared, for example, by homogenizing and sterilizing a sputum specimen by the N-acetyl-L-cysteine-NaOH method (NALC—NaOH method) or the like. The sample is centrifuged and the supernatant is removed. Thereafter, the lysis reagent solution is added to the remaining precipitate (pellet).

The specimen thus lysed may be subjected to a gene amplification process or a gene detection process simply as it is or after being pretreated. Examples of the method of performing the gene amplification or gene detection include a PCR method and modifications of the PCR method, such as a RT-PCR method. Furthermore, examples of the gene to be analyzed include DNA and RNA.

EXAMPLES

Hereinafter, examples of the present invention will be described along with comparative examples. Examples 1-1, 1-2, 1-3, and 1-4 are directed to the first lysis method of the present invention, and Examples 2-1, 2-2, 2-3, and 2-4 are directed to the second lysis method of the present invention.

Example 1-1, Comparative Example 1

A clinical isolate of a tubercule bacillus was cultured in a product Named MycoBroth (Kyokuto Pharmaceutical Industrial Co., Ltd.) at 37° C. until a turbidity corresponding to #1 of the McFarland turbidity standard was obtained. Then, the culture was diluted with phosphate buffer (pH 6.8) so as to achieve a series of 10-fold dilutions ($10^0$-fold to $10^{10}$-fold), thus preparing test solutions containing the tubercule bacillus. Subsequently, 100 µl of the test solutions with the above-described concentrations were poured into screw capped tubes, respectively, and then centrifuged (10000 g, 15 minutes) to prepare pellets. The pellets obtained from the respective test solutions were used as samples to be subjected to a lysis reaction. On the other hand, a product named Triton X-100 (Nacalai Tesque, Inc.) was dissolved in TE buffer (10 mM EDTA and 25 mM Tris-HCl, pH 8.0) so that its concentration became 3 wt % to prepare a lysis reagent solution, and the lysis reagent solution was sterilized by high-pressure steam in an autoclave.

Then, 50 µl of the above-described lysis reagent solution was added to the respective samples, and a lysis treatment was carried out by heating the resultant mixtures at 96° C. for 10 minutes in a heating block. Furthermore, as Comparative Example 1, samples prepared in the same manner as in the above were lysed using a product named AMPLICOR Specimen Pretreatment Kit (Nippon Roche K.K.).

To 37.5 µl of the thus-obtained lysed sample solutions of Example 1-1 and Comparative Example 1, 50 µl of a premixture of a product named AMPLICOR Amplification and Detection Kit (Nippon Roche K.K.) and 12.5 µl of 12 mM magnesium acetate were added. With regard to each of the mixtures obtained, amplification and detection by the PCR method were carried out in a COBAS AMPLICOR in accordance with the operating instructions of the kit.

As a result of the above-described amplification and detection, it was found that, in both Example 1-1 and Comparative Example 1, the samples prepared from the test solutions with a dilution factor of up to $10^7$ were judged as tuberculosis positive and those with a dilution factor of greater than $10^7$ were judged as tuberculosis negative. Thus, it can be said that the lysis method according to Example 1-1 can achieve a sensitivity (lysis efficiency) equivalent to that of the conventional method (Comparative Example 1). Moreover, the lysis method according to Example 1-1 took only half the treatment period of the conventional method (Comparative Example 1).

Example 1-2, Comparative Example 2

A clinical isolate of a tubercule bacillus was cultured in a product named MycoBroth (Kyokuto Pharmaceutical Industrial Co., Ltd.) at 37° C. until a turbidity corresponding to #1 of the McFarland turbidity standard was obtained. Then, the culture was diluted with a non-tuberculous sputum that had been homogenized with a product named SUPTAZYME (Kyokuto Pharmaceutical Industrial Co., Ltd.) so as to achieve a series of 10-fold dilutions ($10^0$-fold to $10^{10}$-fold). The resultant diluents were used as samples. On the other hand, a product named Triton X-100 (Nacalai Tesque, Inc.) was dissolved in TE buffer (10 mM EDTA and 25 mM Tris-HCl, pH 8.0) so that its concentration became 3 wt % to prepare a lysis reagent solution, and the lysis reagent solution was sterilized by high-pressure steam in an autoclave.

Then, 50 µl of the above-described lysis reagent solution was added to the respective samples (100 µl), and a lysis treatment was carried out by heating the resultant mixtures at 96° C. for 10 minutes in a heating block. Furthermore, as Comparative Example 2, samples prepared in the same manner as in the above were lysed using a product named AMPLICOR Specimen Pretreatment Kit (Nippon Roche K.K.).

To 37.5 µl of the thus-obtained lysed sample solutions of Example 1-2 and Comparative Example 2, 50 µl of a premixture of a product named AMPLICOR Amplification and Detection Kit (Nippon Roche K.K.) and 12.5 µl of 12 mM magnesium acetate were added. With regard to each of the mixtures obtained, amplification and detection by the PCR method were carried out in a COBAS AMPLICOR in accordance with the operating instructions of the kit.

As a result of the above-described amplification and detection, it was found that, in both Example 1-2 and Comparative Example 2, the samples with a dilution factor of up to $10^4$ were judged as tuberculosis positive and those with a dilution factor of greater than $10^4$ were judged as tuberculosis negative. Thus, it can be said the lysis method according to Example 1-2 can achieve a sensitivity (lysis efficiency) equivalent to that of the conventional method (Comparative Example 2) even under the influence of contaminants. Moreover, the lysis method according to Example 1-2 took only half the treatment period of the conventional method (Comparative Example 2).

Example 1-3, Comparative Example 3

90 sputum specimens collected from patients were homogenized and sterilized by the NALC—NaOH method ("New Guideline for Tubercle Bacillus Test 2000" edited by The Japanese Society for Tuberculosis). Then, 100 µl of each of the treated sputum specimens was centrifuged at 13,000 g for 10 minutes. After removing the supernatant, the precipitate (pellet) was collected. On the other hand, a product named Triton X-100 (Nacalai Tesque, Inc.) was dissolved in TE buffer (10 mM EDTA and 25 mM Tris-HCl, pH 8.0) so that its concentration became 1 wt % to prepare a lysis reagent solution, and the lysis reagent solution was used after being sterilized by high-pressure steam in an autoclave. Specifically, 50 µl of the sterilized lysis reagent solution was added to the pellets obtained from the respective specimens to suspend the pellets. Then, a lysis treatment was carried out by heating the suspensions at 96° C. for 10 minutes in a heating block. On the other hand, as Comparative Example 3, samples (pellets) prepared in the same manner as in the above were lysed using a product named AMPLICOR Specimen Pretreatment Kit (Nippon Roche K.K.).

To 12.5 µl of the thus-obtained lysed sample solutions of Example 1-3 and Comparative Example 3, 50 µl of a premixture of a product named AMPLICOR Amplification and Detection Kit (Nippon Roche K.K.) and 37.5 µl of 12 mM magnesium acetate were added. With regard to each of the mixtures obtained, amplification and detection by the PCR method were carried out in a COBAS AMPLICOR in accordance with the operating instructions of the kit. In addition, with regard to samples (pellets) prepared in the same manner as in the above, a culture test was carried out in the usual way.

As a result, among the 90 sputum specimens, 41 specimens were judged as tuberculosis positive and 49 specimens were judged as tuberculosis negative when treated by the conventional method (Comparative Example 3). On the other hand, when treated by the first lysis method of the present invention (Example 1-3), 41 specimens were judged as tuberculosis positive and 49 specimens were judged as tuberculosis negative. Thus, the results obtained when treated by the method of Example 1-3 were in exact agreement with those obtained when treated by the conventional method (Comparative Example 3). Moreover, according to the culture test, 42 specimens were judged as tuberculosis positive and 48 specimens were judged as tuberculosis negative, and these results were in approximately 100% (97.8%) agreement with those obtained when treated by the methods of Example 1-3 and Comparative Example 3. Therefore, it can be said that the lysis method of the present invention can produce the lysing effect equivalent to that of the conventional method and can serve as a useful method in actual clinical tests. In addition, the time required for the lysis treatment in the method of Example 1-3 was 30 minutes shorter than that in the method of Comparative Example 3.

Example 2-1, Example 1-4

A product named Lipase G "AMANO" 50 (Amano Pharmaceutical Co., Ltd.) and a product named Lipase AY "AMANO" 30G (Amano Pharmaceutical Co., Ltd.) were dissolved in 10 mM HEPES buffer (pH 7.0) to prepare lipase reagent solutions. Furthermore, a lysis reagent solution was prepared by adding a product named Triton X-100 (Nacalai Tesque, Inc.) to TE buffer (10 mM Tris and 1 mM EDTA, pH 8.0) and sterilizing the mixture by high-pressure steam in an autoclave (the thus-obtained lysis reagent solution is hereinafter referred to as "TE-Triton reagent"). A culture of BCG used for preparing samples was prepared by culturing BCG in a liquid culture medium for growing acid-fast bacteria (a product named MycoBroth, manufactured by Kyokuto Pharmaceutical Industrial Co., Ltd.) until the solution containing the BCG had a turbidity corresponding to #1 of the McFarland turbidity standard and then diluting the solution as necessary.

Thereafter, the resultant solution containing the BCG was diluted gradually ($10^{-4}$, $10^{-3.5}$, $10^{-3}$, $10^{-2.5}$, $10^{-2}$) with phosphate buffer (pH 6.8), thus preparing test solutions. Subsequently, 100 µl of the test solutions with the above-described concentrations were poured into screw capped tubes, respectively, and then centrifuged (10,000 g, 15 minutes) to prepare pellets. The pellets obtained from the respective test solutions were used as samples to be subjected to a lysis reaction. The above-described lipase solutions were prepared so that the lipase concentrations became 100, 500, 1000, 2000, and 3000 (units/ml), respectively. 50 µl of each of the lipase solutions with the above-described concentrations was added to the samples. The resultant mixtures were mixed in a vortex mixer and then centrifuged slightly, followed by incubation at 37° C. for 30 minutes. Next, 50 µl of the TE-Triton reagent (Toriton concentration: 2%) was added to the mixtures, and a lysis treatment was carried out by heating the resultant mixtures at 96° C. for 20 minutes. On the other hand, as Example 1-4, the same procedures were carried out except that the lipase treatment was not performed.

Among 100 µl of each of the lysates obtained through the above-described procedures, 2 µl was used as a template to carry out PCR in order to confirm whether the cells were lysed. The PCR was carried out in the following manner: 94° C. for 1 minute to denature, followed by 30 thermal cycles, each cycle consisting Of 94-C for 30 seconds, 60° C. for 1 minute, and 72° C. for 1 minute. The sequence of the primers and the composition of the reaction solutions are shown below.

| (Composition of PCR Reaction) | |
| --- | --- |
| 10 × Ex-Taq Buffer | 2.5 µl |
| 2.5 mM dNTP Mixture | 2.0 µl |
| 100 µM Primer No. 1 | 0.125 µl (Sequence Number 1) |
| 100 µM Primer No. 2 | 0.125 µl (Sequence Number 2) |

-continued (Composition of PCR Reaction)

| | |
|---|---|
| Ex-Taq (5 u/μL) | 0.125 μl |
| D.W. | 18.125 μl |
| each lysed sample | 2.0 μl |
| Total | 25.0 μl |

With regard to 8 μl of each of the amplification reaction products, electrophoresis was carried out using 3% agarose gel. The results are shown in FIG. 1. The samples supplied to lanes (1) to (7) in FIG. 1 were as follows.
(Explanation of FIG. 1)
(1) The samples only heat-treated in the TE-Triton reagent.
(2) The samples treated with the Lipase G "AMAN" 50 and then heat-treated in the TE-Triton reagent. Lipase concentration: 100 units/ml
(3) The samples treated with the Lipase G "AMAN" 50 and then heat-treated in the TE-Triton reagent. Lipase concentration: 500 units/ml
(4) The samples treated with the Lipase G "AAN" 50 and then heat-treated in the TE-Triton reagent. Lipase concentration: 1,000 units/ml
(5) The samples treated with the Lipase AY "AAN" 30G and then heat-treated in the TE-Triton reagent. Lipase concentration: 100 units/ml
(6) The samples treated with the Lipase AY "AAN" 30G and then heat-treated in the TE-Triton reagent. Lipase concentration: 500 units/ml
(7) The samples treated with the Lipase AY "AAN" 30G and then heat-treated in the TE-Triton reagent. Lipase concentration: 1,000 units/ml
* The mark "M".in FIG. 1 indicates a 100 bp ladder molecular weight marker.
*In each of the regions (1) to (7), the dilution factors of the samples are $10^{-4}$, $10^{-3.5}$, $10^{-3}$, $10^{-2.5}$, and $10^{-2}$ from the left of the lane.

As can be seen from FIG. 1, although a sufficient lysing effect was obtained even when only the heat treatment in the TE-Triton reagent was performed ((1), Example 1-4), still improved lysing effect was obtained when the pretreatment with the lipase was performed ((2) to (7), Example 2-1).

Example 2-2, Example 2-3

The solution containing BCG obtained in the same manner as in the above was diluted gradually ($10^{-4}$, $10^{-3.5}$, $10^{-3}$, $10^{-2.5}$) with phosphate buffer (pH 6.8). The resultant diluents were used as test solutions. Subsequently, 100 μl of the test solutions with the above-described concentrations were poured into screw capped tubes, respectively, and then centrifuged (10,000 g, 15 minutes) to prepare pellets. The pellets obtained from the respective test solutions were used as samples to be subjected to a lysis reaction. On the other hand, Lipase AY "AMANO" 30G was added to the above-described TE-Triton solution so that its concentrations became 500 units/ml to prepare a lysis reagent solution. 100 μl of the lysis reagent solution was added to the samples. The resultant mixtures were mixed in a vortex mixer and then centrifuged slightly, followed by incubation at 45° C. The incubation was carried out for the following two different periods: 10 minutes and 30 minutes. Subsequently, a lysis treatment was carried out by heating the mixtures at 96° C. for 10 minutes (Example 2-2). Furthermore, as Example 2-3, the same procedures were carried out except that the lipase treatment and the heat treatment were performed simultaneously (45° C., 10 minutes).

Among 100 μl of each of the lysates obtained through the above-described procedures, 2 μl was used as a template to carry out PCR in order to confirm whether the cells were lysed. The conditions for carrying out the PCR were the same as those in Example 2-1. With regard to 8 μl of each of the PCR amplification reaction products, whether the cells were lysed was confirmed by carrying out electrophoresis using 3% agarose gel. The results are shown in FIG. 2. The samples supplied to lanes (1) to (5) in FIG. 2 were as follows.
(Explanation of FIG. 2)
(1) The samples subjected to the lipase treatment and the heat treatment Simultaneously in the mixed reagent containing the Lipase AY "AMANO" 30G and the TE-Triton reagent (Example 2-3).
(2) The samples treated with the mixed reagent containing the Lipase AY "AMANO" 30G and the TE-Triton reagent. 45° C., 10 minutes→96° C., 10 minutes
(3) The samples treated with the mixed reagent containing the Lipase AY "AMANO" 30G and the TE-Triton reagent. 45° C., 30 minutes→96° C., 10 minutes
(4) The samples treated with the Lipase AY "AMANO" 30G at 37° C. for 10 minutes and then heat-treated at 96° C. for 10 minutes after the addition of the TE-Triton reagent.
(5) The samples treated with the Lipase AY "AMANO" 30G at 37° C. for 10 minutes and then heat-treated at 96° C. for 10 minutes after the addition of the TE-Triton reagent.
* The mark "M" in FIG. 2 indicates a 100 bp ladder molecular weight marker.
* In each of the regions (1) to (5), the dilution factors of the samples are $10^{-4}$, $10^{-3.5}$, $10^{-3}$, and $10^{-2.5}$ from the left of the lane.

As can be seen from FIG. 2, a sufficient lysing effect was obtained even when the lipolysis treatment and the heat treatment were performed simultaneously (Example 2-3). On the other hand, when the lipolysis treatment and the heat treatment were performed separately (Example 2-2), still improved lysing effect was obtained. The time period for carrying out the incubation did not affect the lysing effect, and no problem arose by dissolving the non-ionic detergent and the lipase in the same buffer.

Example 2-4

Triton X-100 (Nacalai Tesque, Inc.) was added to TE buffer (10 mM Tris and 1 mM EDTA, pH 8.0) and to Tris buffer (10 mM Tris, pH 8.0) so that its concentration became 1%. The resultant mixtures were sterilized in an autoclave, thus preparing a reagent containing EDTA and a reagent containing no EDTA. Hereinafter, these reagents are referred to as a TE-Triton reagent (containing EDTA) and a Tris-Triton reagent (containing no EDTA), respectively. A culture of BCG used for preparing samples was prepared by culturing BCG in a liquid culture medium for growing acid-fast bacteria (a product named MycoBroth, manufactured by Kyokuto Pharmaceutical Industrial Co., Ltd.) until the solution containing the BCG had a turbidity corresponding to #1 of the McFarland turbidity standard and then diluting the solution as necessary.

Thereafter, the resultant solution containing BCG was diluted gradually ($10^{-4.5}$, $10^{-4}$, $10^{-3.5}$, $10^{-3}$, $10^{-2.5}$) with phosphate buffer (pH 6.8), thus preparing test solutions. Subsequently, 100 μl of the test solutions with the above-described concentrations were poured into screw capped tubes, respectively, and then centrifuged (10,000 g, 15 minutes) to prepare pellets. The pellets obtained from the respective test solutions were used as samples to be subjected to a lysis reaction. Lipase AY "AMANO" 30G was added to the above-described TE-Triton solution and to the Tris-Triton solution so that its concentrations became 500 units/ml. Then, 100 μl of each of these solutions was added to the samples. The resultant mixtures were mixed in a vortex mixer and then centrifuged slightly, followed by incubation at 45° C. The incubation was carried out for the following two different periods: 10 minutes and 30 minutes. Subsequently, a heat treatment was carried out by heating the mixtures at 96° C. for 10 minutes.

Among 100 µl of each of the lysates obtained through the above-described procedures, 2 µl was used as a template to carry out PCR in order to confirm whether the cells were lysed. The conditions for carrying out the PCR were the same as those in Example 2-1. With regard to 8 µl of each of the PCR amplification reaction products, whether the cells were lysed was confirmed by carrying out electrophoresis using 3% agarose gel. The results are shown in FIG. 3. The samples supplied to lanes (1) to (6) in FIG. 3 were as follows.

(Explanation of FIG. 3)
(1) to (3): The samples treated with the mixed reagent containing the Lipase AY "AMANO"30G and the TE-Triton reagent (in the presence of EDTA).
45° C., 10 minutes→96° C., 10 minutes
(4) to (6): The samples treated with the mixed reagent containing the Lipase AY "AMANO" 30G and the Tris-triton reagent (in the absence of EDTA).
45° C., 10 minutes→96° C., 10 minutes

* The mark "M" in FIG. 3 indicates a 100 bp ladder molecular weight marker.
* In each of the regions (1) to (6), the dilution factors of the samples are $10^{4.5}$, $10^{-4}$, $10^{-3.5}$, $10^{-3}$, and $10^{-2.5}$ from the left of the lane.

As can be seen from FIG. 3, a sufficient lysing effect was obtained even when EDTA was not used ((4) to (6)). However, a still improved lysing effect was obtained by using EDTA ((1) to (3)).

INDUSTRIAL APPLICABILITY

As specifically described above, the present invention provides a method of securely lysing acid-fast bacteria easily and in a short time without using any special device or special reagent. Therefore, by applying the method of the present invention to, for example, a pretreatment of a sample to be analyzed in an acid-fast bacterium test utilizing gene amplification and detection, the efficiency of the test can be improved easily.

The invention claimed is:

1. A method of amplifying or detecting a gene of an acid-fast bacterium, comprising:
   extracting the gene by lysing the acid-fast bacterium,
   wherein the gene extracting step consists of a lipolysis process in which the acid-fast bacterium is treated with lipase and a heating process in which the acid-fast bacterium is heated in a liquid containing a non-ionic detergent and a metal chelating agent,
   wherein the heating process is performed after the lipolysis process,
   wherein the lipolysis process is performed at pH in a range of 4 to 8 and at a temperature in a range of 37° C. to 60° C. for 5 to 30 minutes, and the heating is performed at a temperature in a range of 37° C. to 100° C. for 5 to 30 minutes, and wherein a concentration of the metal chelating agent is 0.1 to 2.0 mM; and
   at least one step selected from amplifying the gene or detecting the gene by using the extracted gene as it is.

2. The method according to claim 1, wherein the liquid used in the heating process consists of the non-ionic detergent, the metal chelating agent with a concentration of 0.1 to 2.0 mM, and a buffer.

3. The method according to claim 1, wherein the lipolysis process is performed by treating the acid-fast bacterium with a reagent consisting of the lipase and a buffer.

4. The method according to claim 1, wherein the at least one step selected from amplifying the gene or detecting the gene comprises performing the at least one step selected from amplifying the gene or detecting the gene by a method selected from the group consisting of a PCR method and a RT-PCR method.

5. The method according to claim 1, wherein the heating process also serves to deactivate the lipase.

6. The method according to claim 1, wherein the lipolysis process and the heating process are performed in a buffer.

7. The method according to claim 1, wherein the lipolysis process and the heating process are performed in a same container as a closed system.

SEQUENCE LISTING

<160> NUMBER OF SEQ ID NOS: 2

<210> SEQ ID NO 1
<211> LENGTH: 16
<212> TYPE: DNA
<213> ORGANISM: Artificial Sequence
<220> FEATURE:
<223> OTHER INFORMATION: Primer No.1

<400> SEQUENCE: 1
tcgtccagcg ccgctt                                                    16

<210> SEQ ID NO 2
<211> LENGTH: 20
<212> TYPE: DNA
<213> ORGANISM: Artificial Sequence
<220> FEATURE:
<223> OTHER INFORMATION: Primer No.2

<400> SEQUENCE: 2
caaaggccac gtaggcgaac                                                20

8. The method according to claim 6, wherein a concentration of the lipase in the buffer is 10 to 10000 units/ml.

9. The method according to claim 1, wherein the non-ionic detergent is at least one selected from the group consisting of D-sorbitol fatty acid esters, polyoxyethyleneglycol sorbitan alkyl esters, and polyoxyethyleneglycol p-t-octylphenyl ethers.

10. The method according to claim 6, wherein a concentration of the non-ionic detergent in the buffer is 0.01 to 10 wt %.

11. The method according to claim 1, wherein the metal chelating agent is at least one selected from the group consisting of ethylenediaminetetraacetic acid (EDTA), glycol ether diaminetetraacetic acid (EGTA), and 1,2-cyclohexanediaminetetraacetic acid (CyDTA).

12. The method according to claim 1, wherein the acid-fast bacterium to be lysed is at least one selected from the group consisting of *M avium, M. intracellularae, M. gordonae, M. tuberculosis, M. kansasii, M. fortuitum, M. chelonae, M. bovis, M. scrofulaceum, M. paratuberculosis, M. phlei, M. marinum, M. simiae, M. szulgai, M. leprae, M. xenopi, M. ulcerans, M. lepraemurium, M. flavescens, M terrae, M nonchromogenicum, M. malmoense, M. asiaticum, M. vaccae, M. gastri, M. triviale, M. haemophilum, M. africanum, M. thermoresistable*, and *M. smegmatis*.

13. The method according to claim 1, wherein a biological sample containing the acid-fast bacterium is at least one selected from the group consisting of sputum, spinal fluid, feces, saliva, blood, tissues, swab, liquid obtained by gastrolavage, and urine.

* * * * *